(12) United States Patent
Harper et al.

(10) Patent No.: US 7,731,943 B2
(45) Date of Patent: Jun. 8, 2010

(54) STABILIZED AQUEOUS ALUMINUM ZIRCONIUM SOLUTIONS

(75) Inventors: Thomas L. Harper, Middletown, NY (US); Allan Rosenberg, South Orange, NJ (US); Shailesh Mehta, Port Jervis, NY (US)

(73) Assignee: Summit Research Labs, Inc., Huguenot, NY (US)

(*) Notice: Subject to any disclaimer, the term of this patent is extended or adjusted under 35 U.S.C. 154(b) by 694 days.

(21) Appl. No.: 11/129,072

(22) Filed: May 13, 2005

(65) Prior Publication Data

US 2006/0008435 A1 Jan. 12, 2006

Related U.S. Application Data

(60) Provisional application No. 60/585,901, filed on Jul. 7, 2004.

(51) Int. Cl.
*A61K 8/28* (2006.01)
*A61K 8/58* (2006.01)

(52) U.S. Cl. .......................... 424/66; 424/68; 424/401; 424/663; 424/685

(58) Field of Classification Search .............. 424/401, 424/68, 66
See application file for complete search history.

(56) References Cited

U.S. PATENT DOCUMENTS

| 2,854,382 A * | 9/1958 | Grad .................... 424/66 |
| 2,889,253 A * | 6/1959 | Berger et al. ............... 424/66 |
| 5,118,497 A | 6/1992 | Katsoulis |
| 5,202,123 A | 4/1993 | Katsoulis |
| 5,225,187 A | 7/1993 | Carmody |
| 5,380,450 A * | 1/1995 | Conway et al. ............. 252/75 |
| 5,589,196 A | 12/1996 | Callaghan et al. |
| 5,672,340 A | 9/1997 | Sun et al. |
| 5,770,186 A | 6/1998 | Callaghan et al. |
| 5,972,321 A * | 10/1999 | Kligerman et al. ............ 424/65 |
| 6,066,314 A * | 5/2000 | Tang et al. .................. 424/65 |
| 6,375,937 B1 * | 4/2002 | Chopra et al. ................ 424/65 |
| 6,387,357 B1 | 5/2002 | Chopra et al. |
| 6,403,069 B1 | 6/2002 | Chopra et al. |
| 6,517,819 B1 * | 2/2003 | Breker et al. ................. 424/65 |
| 6,726,901 B2 | 4/2004 | Yin et al. |
| 6,783,755 B2 | 8/2004 | Kajino et al. |
| 6,835,374 B2 | 12/2004 | Parekh et al. |
| 2003/0021757 A1 | 1/2003 | Carillo et al. |
| 2003/0211060 A1 | 11/2003 | Yin et al. |
| 2003/0232026 A1 * | 12/2003 | Kajino et al. ................ 424/66 |
| 2004/0001795 A1 | 1/2004 | Li et al. |
| 2004/0022750 A1 | 2/2004 | Lee et al. |
| 2004/0136934 A1 | 7/2004 | Carrillo et al. |
| 2005/0019287 A1 | 1/2005 | Li et al. |

OTHER PUBLICATIONS

Barel et al., Handbook of Cosmetic Science and Technology, 2001, Informa Health Care, p. 691.*
Williams et al., Chemistry and Technology of the Cosmetics and Toiletries Industry, 1992, Springer, p. 322.*
Varshney, K.G., Synthesis and Characterization of Zirconium Aluminophosphate. A New Cation Exchanger, Langmuir, 1998, 14, 7353-7358.*
Physical Organic Chemistry, Jack Hine, pp. 296-299, McGraw Hill (1962).

* cited by examiner

*Primary Examiner*—Johann R Richter
*Assistant Examiner*—Danielle Sullivan
(74) *Attorney, Agent, or Firm*—Caesar, Rivise, Bernstein, Cohen & Pokotilow, Ltd.

(57) ABSTRACT

The present invention describes a method and compositions by which introducing $PO_4^{-3}$ ion at particular stage in the preparation of aluminum/zirconium solutions surprisingly results in significantly improved zirconium molecular weight stability.

14 Claims, No Drawings

STABILIZED AQUEOUS ALUMINUM ZIRCONIUM SOLUTIONS

CROSS REFERENCE TO RELATED APPLICATIONS

This utility application claims the benefits under 35 U.S.C. §199(e) Provisional Application Ser. No. 60/585,901 filed on Jul. 7, 2004 entitled STABILIZED AQUEOUS ALUMINUM ZIRCONIUM SOLUTIONS and whose entire disclosure is incorporated by reference herein.

BACKGROUND OF THE INVENTION

1. Field of Invention

This invention relates generally to the field of stabilized aqueous aluminum zirconium solutions useful in antiperspirant formulations, methods of making same and compositions thereof.

2. Description of Related Art

Aluminum zirconium chlorohydrate-glycine aqueous solutions are used in various antiperspirant formulations as the active ingredient. It is known that lower molecular weight zirconium polymers are more efficacious than larger molecular weight zirconium polymers. In these solutions and in the formulas (i.e., clear gels) these materials rapidly polymerize, reducing their effectiveness.

The following references are disclosed. U.S. Pat. No. 5,118,497 (Katsoulis), U.S. Pat. No. 5,202,123 (Katsoulis), U.S. Pat. No. 5,225,187 (Carmody), U.S. Pat. No. 5,589,196 (Callaghan et al.), U.S. Pat. No. 5,672,340 (Sun et al.), U.S. Pat. No. 5,770,196 (Callaghan et al.), U.S. Pat. No. 6,403,069 (Chopra et al), U.S. Pat. No. 6,726,901 (Yin et al.), U.S. Pat. No. 6,783,755 (Kajino et al.), U.S. Pat. No. 6,835,374 (Parekh et al.), U.S. Publication No. 2003/0021757 (Carillo et al.), U.S. Publication No. 2003/0211060 (Yin et al.), U.S. Publication No. 2004/00011795 (Li et al.), U.S. Publication No. 2004/022750 (Lee et al.), U.S. Publication No. 2004/0136934 (Carrillo et al.), U.S. Publication No. 2005/0019287 (Li et al.).

BRIEF SUMMARY OF THE INVENTION

The present invention describes compositions of, and a method for making the compositions, where introducing a phosphate ion such as $PO_4^{-3}$, at a certain stage in the preparation of the Aluminum/Zirconium (Al/Zr) solutions surprisingly results in significantly improved zirconium molecular weight stability.

DETAILED DESCRIPTION OF THE INVENTION

The present invention describes various methods of introducing a phosphate $(PO_4^{-3})$ ion at a certain stage in the preparation of the Al/Zr solutions which surprisingly results in significantly improved zirconium molecular weight stability. The present invention is directed to such methods, compositions thereof, and methods of using same in compositions such as in antiperspirant compositions and the like.

Method:

A phosphate ion, such as $PO_4^{-3}$, is to introduced in the initial dissolution of the zirconium salt.

The phosphate $(PO_4^{-3})$ to zirconium ratio should be approximately weight/weight 0.02:1-0.151:1.

The $PO_4^{-3}$ ion may be from $H_3PO_4$ or a variety of salts; for example, $Na_3PO_4$, $K_3PO_4$, etc. and the invention is not intended on being limited to any particular salt.

Several routes of manufacture for stabilized Al/Zr solutions are disclosed in the present invention: one utilizing Zirconium Carbonate paste $(Zr(CO_3)_2)$ or another source or zirconium ion, another utilizing Zirconium Oxychloride $(ZrOCl_2)$ or another source of zirconium ion.

1. An Example of the $Zr(CO_3)_2$ Route:

Combine 35.88 grams of 20° baume HCl and 0.5 grams 85% $H_3PO_4$

Combine $HCl/H_3PO_4$ mixture with 64.1 grams of $Zr(CO_3)_2$ paste.

Mix well. Once dissolved, allow to stand at about room temperature for approximately 24 hours.

To the zirconium solution add buffer (preferably a glycine buffer) at a molar ratio of approximately 1:1 with zirconium.

The zirconium solution may now be combined with an aqueous aluminum salt to a desired Al:Zr molar ratio which may be about 1:1 to about 11:1, and preferably about 2:1 to about 10:1.

2. An Example of the $ZrOCl_2$ Route:

Combine 50 grams $H_2O$+0.5 grams 85% $H_3PO_4$

Add 50 grams $ZrOCl_2$ crystals. Mix well. Allow to sit for 24 hours once dissolved.

To the zirconium solution add a buffer (preferably glycine) at a molar ratio of approximately 1:1 with zirconium.

The zirconium solution may now be combined with an aqueous aluminum salt to a desired Al:Zr molar ratio previously specified and a desired (Al+Zr):Cl molar ratio. The desired (Al+Zr):Cl molar ratio is in the approximate range of about 0.2:1 to about 2.5:1, preferably about 0.9:1 to about 2.1:1.

The order of addition when preparing the final Al/Zr solution should be:

1. Zr solution
2. Aluminum solution
3. Acid/water

We have made the following observations using a Wyatt Dawn Light Scattering instrument to measure zirconium molecular weight in Al/Zr glycine aqueous solutions.

Freshly prepared Al/Zr solution: no $PO_4^{-3}$ has a molecular weight of 18,000. Within 24 hours, the molecular weight increases to 50,000.

In contrast, a freshly prepared Al/Zr solution containing $PO_4^{-3}$ ion has a molecular of 18,000 after 24 hours, no molecular weight increase is noted. The monitoring of the molecular weight for one month shows an increase to only 30,000 molecular weight.

Polymerically Stable Zirconium Salts

Zirconium salts and aqueous solutions of these salts are used in a variety of applications, including antiperspirants, oil field applications, catalysts, ceramics, electronics, leather tanning, textile dyeing, paper manufacturing, and production of other zirconium chemicals. Zirconium salts consist of zirconium polymeric species of varying distribution. The distributions of these polymers have a significant impact on the salts performance in said application. Further, zirconium salts and especially the aqueous solutions of these salts are not stable with respect to this polymer distribution.

We describe a method to produce a polymerically stabilized zirconium carbonate paste by introducing phosphate $(PO_4^{-3})$ ion at a particular proper stage in the preparation of the zirconium carbonate paste. This stabilized zirconium carbonate may then be further processed to produce other stable zirconium salts and stable aqueous solutions of these salts.

We also describe various methods by which a molecular weight stable aluminum zirconium chlorohydrate glycine aqueous solution for use in antiperspirants can be produced by the addition of a phosphate ion (e.g., $PO_4^{-3}$) ion at a certain stage of manufacture. These solutions may then be used as solutions or dried to produce a powder. It is known that lower molecular weight zirconium polymers are more effective in the reduction of perspiration than are larger molecular weight zirconium polymers. It is also known that zirconium in aqueous solutions and the formulations (i.e., clear gels) they are used in rapidly polymerize resulting in reduced effectiveness. The dried form of these salts also exhibit polymerization to a lesser extent than solutions.

Method:

We describe several processes to produce polymerically stable zirconium carbonate.

1. Zirconium Oxychloride ($ZrOCl_2$) Route:

A solution containing one or more of the following bases is prepared: ammonium carbonate, ammonium bicarbonate, sodium carbonate, sodium bicarbonate. A solution of zirconium oxychloride is prepared and $PO_4^{-3}$ ion is added using phosphoric acid or a $PO_4^{-3}$ containing salt. The $PO_4^{-3}$ content should be in a molar ratio of P:Zr of 0.01:1-0.15:1. The zirconium solution is then added to the base solution with mixing, heating, and then pH adjustment to precipitate zirconium carbonate. The approximate heating temperature is about 50-120 degrees C. with a heating time of about 1-3 hours. The pH should be adjusted between about 2.0 and about 7.0 and be stable for 30 minutes at the final reading. The zirconium carbonate should be washed and then separated from the liquid.

2. Zirconium Sulfate Route:

A solution containing one or more of the following bases is prepared: ammonium carbonate, ammonium bicarbonate, sodium carbonate, sodium bicarbonate. The base concentration should be in the approximate range of about 1-15% as $CO_3$. A solution of zirconium sulfate is prepared and the $PO_4^{-3}$ ion is added using phosphoric acid or a $PO_4^{-3}$ containing salt. The $PO_4^{-3}$ content should be in a molar ratio of P:Zr of about 0.01:1-0.15:1. The zirconium solution is then added to the base solution with mixing, heating, and pH adjustment to precipitate zirconium carbonate. Zirconium carbonate should be washed and then separated from liquid.

We describe several methods for the manufacture of stabilized Al/Zr solutions:

1. Zirconium Carbonate Route:

Combine 35.88 grams 20 baume HCl and 0.5 grams 85% $H_3PO_4$.

Combine $HCl/H_3PO_4$ mixture with 64.1 grams zirconium carbonate paste.

Mix well and allow to sit for approximately 24 hours.

To the zirconium solution add a buffer (preferably a glycine buffer) at a glycine:zirconium molar ratio of about 0.51-1.5:1.

The zirconium solution may now be combined with an aqueous aluminum salt to the desired to Al:Zr molar ratios and (Al+Zr): Cl molar ratios identified above (note always add the aluminum to the zirconium). The solution may be used as is or dried in conventional means to form a powder.

2. Zirconium Oxychloride Route:

Combine 50 grams water and 0.5 grams 85% $H_3PO_4$.

Add 50 grams of zirconium oxychloride. Mix well. Let sit for approximately 24 hours.

To the zirconium solution add a buffer (preferably glycine) at a glycine:zirconium molar ratio of 0.5:1 to 1.5:1.

The zirconium solution may now be combined with an aqueous aluminum salt to the desired Al:Zr molar ratios and (Al+Zr):Cl molar ratios previously described. (Note, always add aluminum to zirconium). The solution may be used as is or dried in a conventional manner to form a powder.

We have made the following observations on the above Al/Zr solutions using a Wyatt Dawn Light Scattering instrument.

Freshly prepared Al/Zr solutions with or without $PO_4^{-3}$ ion have a molecular weight of 18,000. The solution not containing $PO_4^{-3}$ shows an increase in molecular weight to 50,000 in 24 hours. In contrast, the solution containing $PO_4^{-3}$ does not increase in 24 hours and shows an increase to only 30,000 after 30 days.

Without further elaboration the foregoing will so fully illustrate our invention that others may, by applying current or future knowledge, adapt the same for use under various conditions of service.

What is claimed is:

1. A stabilized aqueous solution composition comprising aluminum ion, zirconium ion, phosphate ion, and chloride ion, wherein the phosphate ion to zirconium ion ratio is about 0.02:1-0.151:1 weight/weight, further wherein the zirconium is polymerically stable.

2. The composition of claim 1 wherein the phosphate ion is $PO_4^{-3}$.

3. The composition of claim 1 wherein (Al+Zr):Cl is present in a molar ratio of about 0.3:1 to about 2.5:1.

4. The composition of claim 3 wherein the phosphate ion is $PO_4^{-3}$.

5. A stabilized aqueous solution composition comprising aluminum ion, zirconium ion, phosphate ion, glycine and chloride ion, wherein the glycine is at a molar ratio of about 0.5:1 to 1.5:1 with zirconium ion, and wherein Al:Zr is present in a molar ratio of about 1:1 to about 11:1, further wherein the zirconium is polymerically stable.

6. A stabilized aqueous solution composition comprising aluminum ion, zirconium ion, and phosphate ion, wherein the phosphate ion to zirconium ion ratio is about 0.02:1-0.151:1 weight/weight, further wherein the zirconium is polymerically stable.

7. A stabilized aqueous solution composition comprising aluminum ion, zirconium ion, phosphate ion, and chloride ion, made by the method comprising the steps of: (a) combining a chloride-containing acid and a source of phosphate ion to form a phosphate mixture; (b) combining the phosphate mixture with a zirconium ion source and mixing well to dissolve; (c) allowing the product of step (b) to stand at about room temperature for about 24 hours; (d) mixing a buffer at a molar ratio of about 1:1 with zirconium; (e) combining the product of step (d) with aqueous aluminum salt to an Al:Zr molar ratio of about 1:1 to about 11:1 and an (Al+Zr):Cl molar ratio of about 0.3:1 to about 2.5:1; and (f) optionally, drying to form a powder, further wherein the zirconium is polymerically stable.

8. The composition of claim 7 wherein the phosphate ion to zirconium ion ratio is about 0.02:1-0.151:1 weight/weight.

9. The composition of claim 7 wherein the zirconium ion source is a $Zr(CO_3)_2$ paste.

10. The composition of claim 7 wherein the zirconium ion source is zirconium oxychloride.

11. The composition of claim 7 wherein the buffer is a glycine buffer.

12. The composition of claim 7 wherein the phosphate ion is $PO_4^{-3}$.

13. The composition of claim 7 wherein the Al:Zr molar ratio is about 2:1 to about 10:1.

14. The composition of claim 7 wherein the (Al+Zr):Cl molar ratio is about 0.9:1 to about 2.1:1.

* * * * *